(12) United States Patent
Ouchi

(10) Patent No.: US 6,440,062 B1
(45) Date of Patent: Aug. 27, 2002

(54) CONTROL WIRE DRIVING MECHANISM FOR USE IN ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 33 days.

(21) Appl. No.: 09/696,943

(22) Filed: Oct. 27, 2000

(30) Foreign Application Priority Data

Nov. 10, 1999 (JP) .......................................... 11-319134
Feb. 28, 2000 (JP) ...................................... 2000-050666

(51) Int. Cl.⁷ .............................................. A61B 1/005
(52) U.S. Cl. ...................................... 600/146; 600/147
(58) Field of Search ................................ 600/146, 147, 600/149

(56) References Cited

U.S. PATENT DOCUMENTS

| 4,203,430 A | 5/1980 | Takahashi |
| 4,236,509 A | 12/1980 | Takahashi et al. |
| 4,483,326 A * | 11/1984 | Yamaka et al. ............. 600/141 |
| 4,617,914 A | 10/1986 | Ueda |
| 4,741,335 A * | 5/1988 | Okada ........................ 606/127 |
| 5,359,994 A * | 11/1994 | Krauter et al. .............. 600/109 |
| 5,752,912 A | 5/1998 | Takahashi et al. |

FOREIGN PATENT DOCUMENTS

| JP | 62-23446 | 6/1987 |
| JP | 63-5683 | 2/1988 |
| JP | 3-3483 | 1/1991 |
| JP | 4-16644 | 4/1992 |
| JP | 5-46404 | 12/1993 |

* cited by examiner

Primary Examiner—Stephen M. Hepperle
(74) Attorney, Agent, or Firm—Greenblum & Bernstein, P.L.C.

(57) ABSTRACT

A control wire driving mechanism for use in an endoscope includes a toothed wheel actuated to rotate in a control part of the endoscope. A control wire has a cord-like member helically wound on and secured to the outer peripheral surface of a portion near the proximal end thereof at a pitch corresponding to the pitch of the toothed wheel. The control wire is meshed with the toothed wheel at the portion wound with the cord-like member.

11 Claims, 11 Drawing Sheets

PULL

CONTROL WIRE DRIVING MECHANISM FOR USE IN ENDOSCOPE

BACKGROUND OF THE INVENTION

The present disclosure relates to subject matter contained in Japanese Patent Application No. 11-319134 (filed on Nov. 10, 1999) and Japanese Patent Application No. 2000-50666 (filed on Feb. 28, 2000), which are expressly incorporated herein by reference in their entireties.

1. Field of the Invention

The present invention relates to a control wire driving mechanism for use in an endoscope to pull a control wire by rotation of a rotating member.

2. Description of the Prior Art

There has heretofore been known a control wire driving mechanism for use in a bending control device of an endoscope, for example. In the mechanism, a pinion (i.e. a toothed wheel) that is actuated to rotate with a control knob (or a control lever) is meshed with a rack connected to the proximal end of a control wire, and the rack is advanced or retracted linearly by rotating the pinion, thereby driving the control wire to advance or retract.

However, such a rack-and-pinion mechanism needs a space for travel of the rack on each of the front and rear sides of the pinion as viewed in the axial direction of the control wire. The necessary rack travel space is twice as long as the travel stroke of the control wire.

For this reason, the control knob cannot be disposed closer to the upper end of the control part. Consequently, it is impossible to ensure a sufficient length for the grip portion of the control part. This causes operability to be impaired.

In view of the above-described problem, one type of bending control device for an endoscope is arranged such that the proximal end portion of a control wire is wound on a pulley having a circumferential groove formed on the entire periphery thereof, and the control wire is pulled by rotation of the pulley. Such a pulley can be disposed closer to the upper end of the control part of the endoscope.

In such a mechanism, however, the end portion of the control wire must be secured to the pulley. Therefore, the maximum angle of rotation is limited considerably, and the control wire is likely to break owing to the stress concentration on the secured portion of the control wire.

Under these circumstances, a mechanism using a sprocket wheel as a rotating member has been put to practical use and widely used. In the mechanism, a chain connected to the proximal end of a control wire is meshed with the sprocket wheel to pull the control wire.

However, because the chain has a considerable thickness and height, the device becomes large and heavy when the chain is connected to the proximal end of the control wire, and hence the endoscope control part becomes unfavorably large and heavy. This gives rise to a problem because it is necessary for the operator to actuate the endoscope control part while holding it with his/her hand throughout the observation of the inside of a body cavity. In addition, the use of a chain causes the cost to rise unfavorably.

SUMMARY OF THE INVENTION

An object of the present invention is to provide a control wire driving mechanism for use in an endoscope in which a toothed wheel can be disposed at a position closer to the upper end of a control part of the endoscope, so that it is possible to ensure a sufficient length for the grip portion and hence possible to attain favorable operability, and which can be formed in an extremely simple, compact and lightweight structure at reduced cost and is also superior in function.

Other objects and advantages of the present invention will become apparent from the following detailed description of illustrated embodiments of the invention.

According to the present invention, there is provided a control wire driving mechanism for use in an endoscope. The control wire driving mechanism includes a toothed wheel actuated to rotate in a control part of the endoscope. A control wire has a cord-like member helically wound on and secured to the outer peripheral surface of a portion near the proximal end thereof at a pitch corresponding to the pitch of the toothed wheel. The control wire is meshed with the toothed wheel at the portion wound with the cord-like member.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Figure 1:
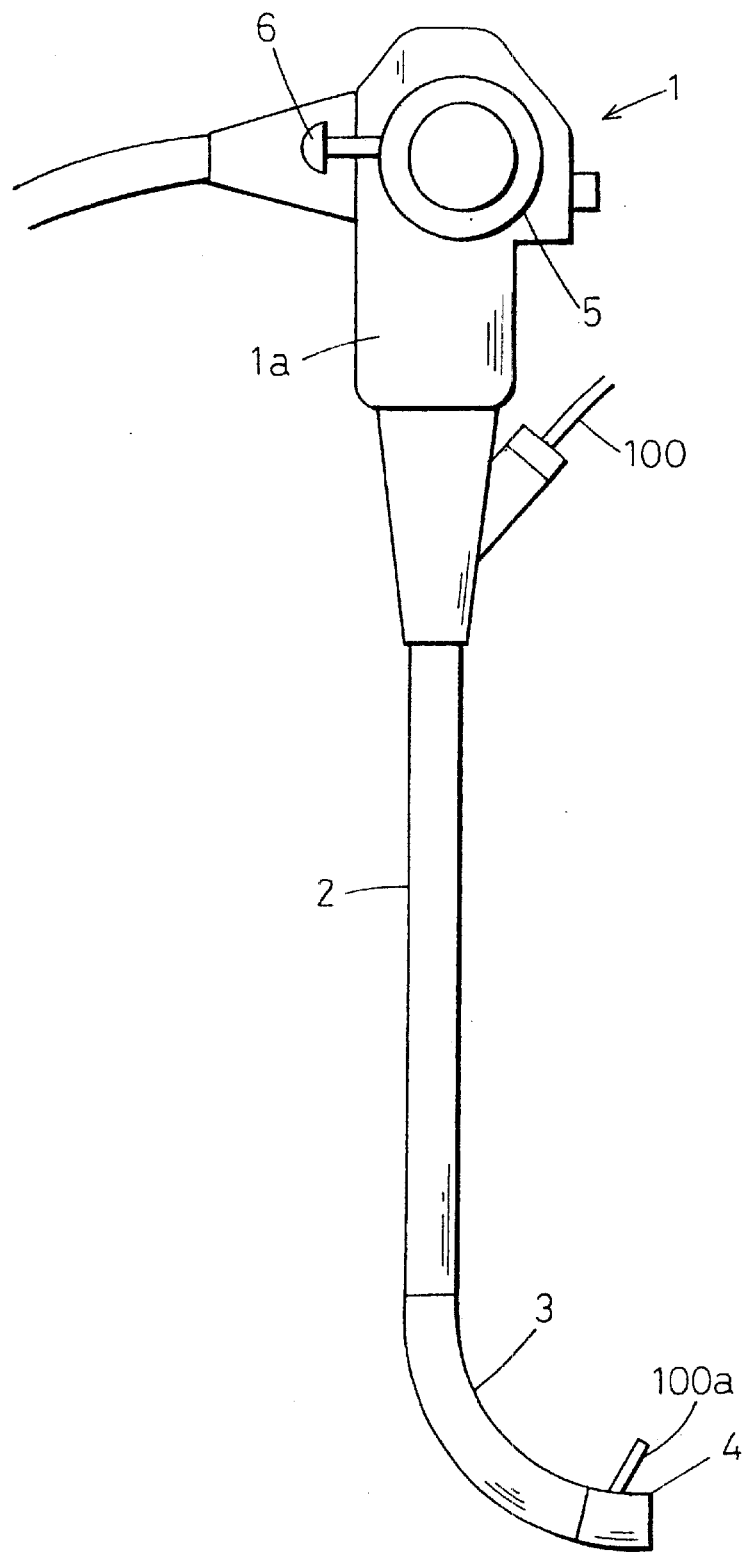
FIG. 1 is an external view showing the whole arrangement of an endoscope to which the present invention is applied.

FIG. 1 shows the whole arrangement of an endoscope.

The endoscope has a control part 1 adapted to be held by an operator with his/her hand when operating the endoscope.

A flexible tube 2 is connected to the lower end of the control part 1 to form an insert part of the endoscope.

A bendable portion 3 is connected to the distal end of the flexible tube 2. The bendable portion 3 can be bent as desired by remote control. A distal end block 4 is connected to the distal end of the bendable portion 3. The distal end block 4 contains an objective optical system or the like.

A bending control knob 5 is provided on the upper half of the control part 1 to control bending of the bendable portion 3. A portion of the control part 1 below the bending control knob 5 is a grip portion 1a. An erecting member control lever 6 is used to change remotely the direction of projection of a distal end portion 10a of a treating instrument 100 inserted into an instrument-inserting channel of the endoscope.

Figure 2:
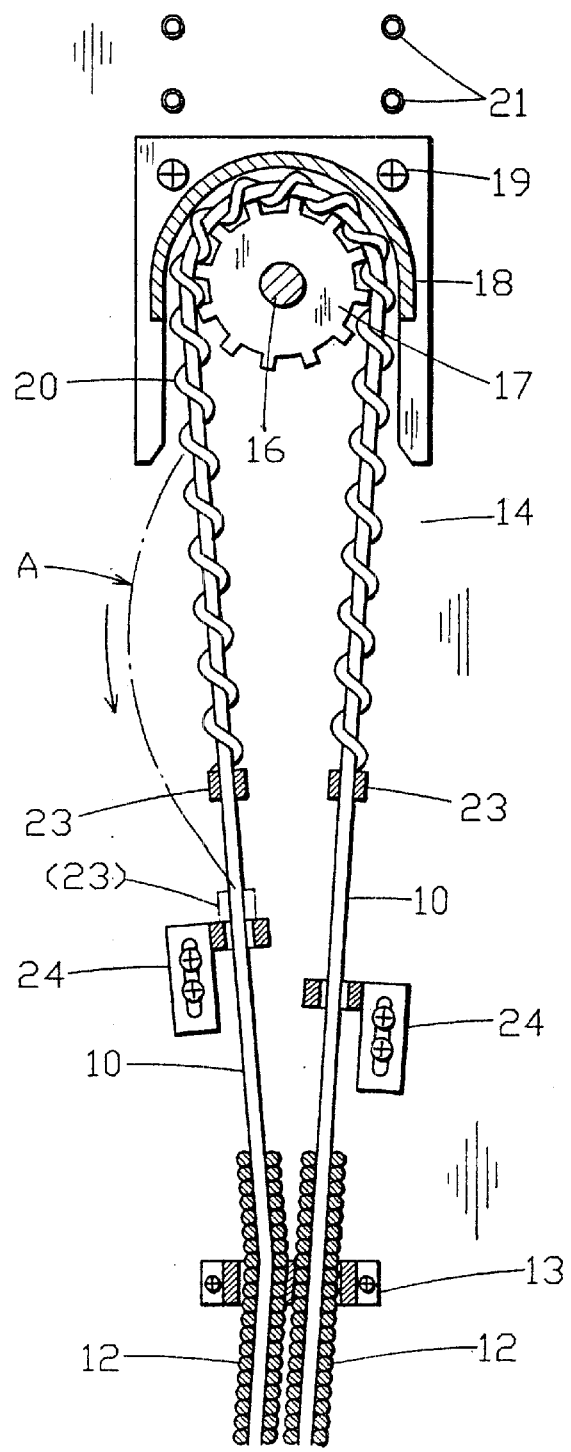
FIG. 2 is a sectional view of a bending control wire driving mechanism according to a first embodiment of the present invention.

FIG. 2 shows a bending control wire driving mechanism provided in the control part 1 to pull a control wire 10 for bending the bendable portion 3.

A pair of control wires 10 are connected at their distal ends to the distal end of the bendable portion 3. Intermediate portions of the control wires 10 are axially movably passed through respective guide pipes 12. The guide pipes 12 are formed from close-wound coil pipes inserted in the flexible tube 2, which forms the insert part of the endoscope. The proximal ends of the control wires 10 are led into the control part 1.

Although in this embodiment the proximal ends of a pair of control wires 10 are joined together to form a single wire as a whole, the arrangement may be such that control wire portions that are passed through the guide pipes 12 and a wire portion disposed in the control part 1 are formed separately from each other and connected together in the control part 1. A securing seat 13 secures the proximal end portions of the guide pipes 12 to a frame 14 in the control part 1.

A toothed wheel 17 is connected directly to a shaft 16 driven to rotate with the bending control knob 5. A U-shaped curved portion of the control wire 10 within the control part 1, which is formed by the interconnected proximal end portions of the pair of control wires 10, is wound approximately half around the toothed wheel 17.

A cord-like member 20 is helically wound on and secured to the outer peripheral surface of the control wire 10 at the same pitch as the pitch of the toothed wheel 17, so that the teeth of the toothed wheel 17 mesh with the gaps between the turns of the cord-like member 20.

Figure 3:
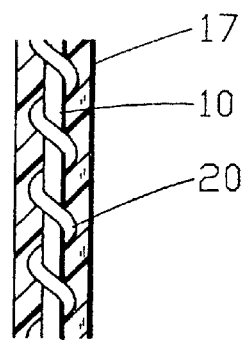
FIG. 3 is a fragmentary view of a control wire and a toothed wheel meshed therewith in the first embodiment of the present invention as seen from the tip side.

Accordingly, the toothed wheel 17 is, as shown in FIG. 3, a helical gear having teeth formed obliquely in the same direction as the direction of the helically wound cord-like member 20. The toothed wheel 17 may have any tooth form as long as the teeth of the toothed wheel 17 will not undesirably disengage from the gaps between the turns of the cord-like member 20. With this arrangement, the toothed wheel 17 is allowed to mesh with the control wire 10 at any rotational position thereof. Accordingly, the bending control wire driving mechanism can be assembled with a high degree of freedom.

Referring back to FIG. 2, an outer surface cover 18 is secured to the frame 14 with machine screws 19 to surround the portion of the control wire 10 wound with the cord-like member 20 so that the control wire 10 will not undesirably disengage from the toothed wheel 17. Threaded holes 21 are provided so that the outer surface cover 18 can be secured to the frame 14 at a position shifted from the illustrated position.

By virtue of the described arrangement, when the toothed wheel 17 is rotated by turning the bending control knob 5, the control wires 10 move axially as the teeth of the toothed wheel 17 move. Thus, one of the pair of control wires 10 is pulled, while the other is pushed out. Consequently, the bendable portion 3 bends at an angle corresponding to the amount by which one of the control wires 10 is pulled. Because the bending control wire driving mechanism requires substantially no space for the bending operation above the toothed wheel 17, it is possible to dispose the toothed wheel 17 and the bending control knob 5, which is connected to the toothed wheel 17, at a position closer to the upper end of the control part 1 and hence possible to ensure a sufficient length for the grip portion 1a of the control part 1.

The cord-like member 20 is wound on the control wire 10 over a length sufficient to keep the cord-like member 20 from disengaging from the toothed wheel 17 even when the bendable portion 3 is bent to the maximum. Travel stoppers 23 are secured to the control wire 10 at both ends of the cord-like member 20 wound thereon.

Fixed stoppers 24 are so arranged that the travel stopper 23 attached to the payout-side control wire 10 abuts on the associated fixed stopper 24. If the bending operation is further performed after the travel stopper 23 has abutted on the fixed stopper 24, as shown by A in the figure, the payout-side control wire 10 deflects considerably in the control part 1.

Figure 4:
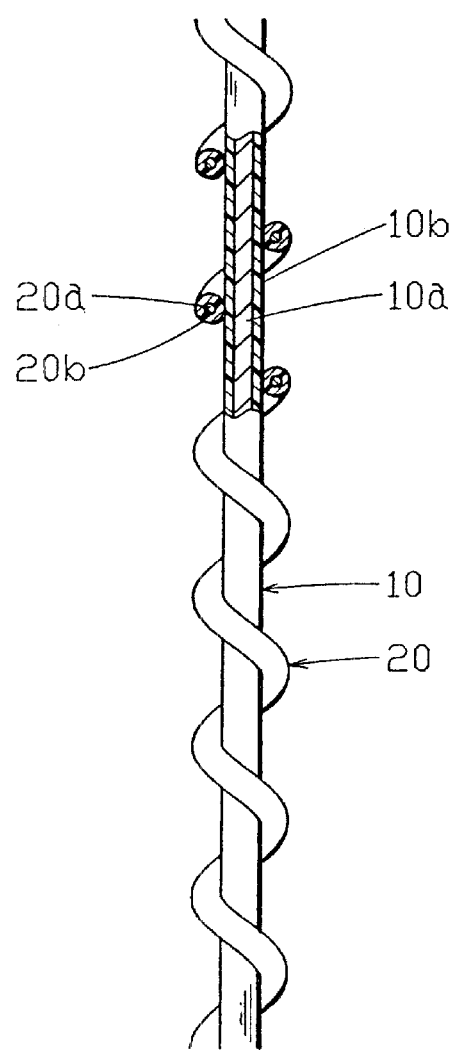
FIG. 4 is a partly-sectioned enlarged side view of the control wire in the first embodiment of the present invention.

In the present invention, any fixing method may be used to secure the cord-like member 20 to the control wire 10. For example, as shown in FIG. 4, metal wires 10a and 20a that are used to form the control wire 10 and the cord-like member 20 are provided with coatings 10b and 20b of a thermoplastic synthetic resin material (e.g. a polyamide resin or a polyurethane resin) to a thickness of about 0.1 to 0.3 mm. Then, the cord-like member 20 is wound around the control wire 10, and in this state, the control wire 10 and the cord-like member 20 are heated to weld together the coatings 10b and 20b.

The metal wire 10a used for the control wire 10 may be a stainless-steel stranded wire with a diameter of the order of from 0.3 mm to 1 mm, e.g. a 1×7 stranded wire or a 1×3 stranded wire. The outer diameter of a portion of the control wire 10 that is wound with the cord-like member 20 should preferably be within about 3 to 5 times the diameter of the metal wire 10a (e.g. about 1 to 5 mm). In the case of an industrial endoscope that may be inserted into a pipe bore with a large diameter, the diameter of the control wire 10 should be increased according to use conditions.

Figure 5:
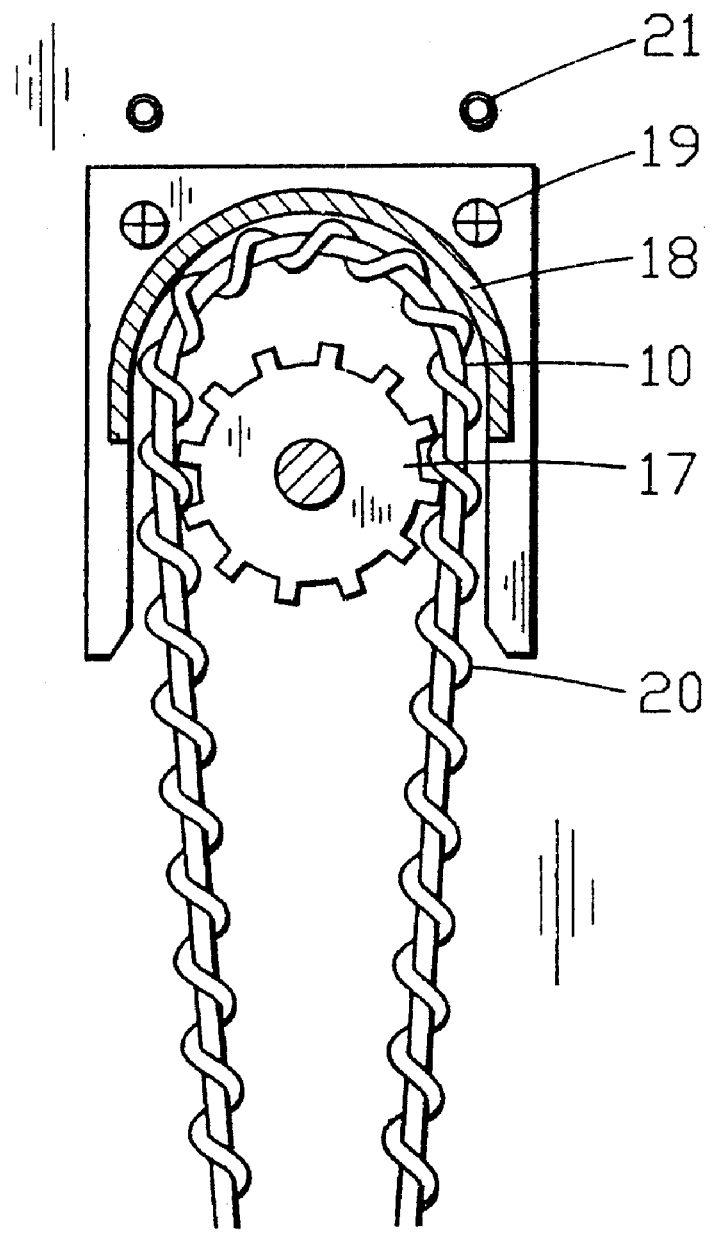
FIG. 5 is a fragmentary sectional view of the bending control wire driving mechanism according to the first embodiment of the present invention.

The control wire 10 elongates gradually as it is pulled repeatedly in use of the endoscope. In the mechanism according to the present invention, however, no slip occurs in the engagement of the control wire 10 with the toothed wheel 17. Therefore, the mechanism operates reliably. However, the maximum angle of bending of the bendable portion 3 may decrease as the control wire 10 is pulled repeatedly. In such a case, as shown in FIG. 5, the securing position of the outer surface cover 18 should be moved to shift the mesh position of the control wire 10 with respect to the toothed wheel 17. The same measures may be taken when the control wire 10 is excessively long, for example, at the time of initial assembly.

It should be noted that two mechanisms as stated above may be combined together for use in a four-direction bending control device.

Figure 6:
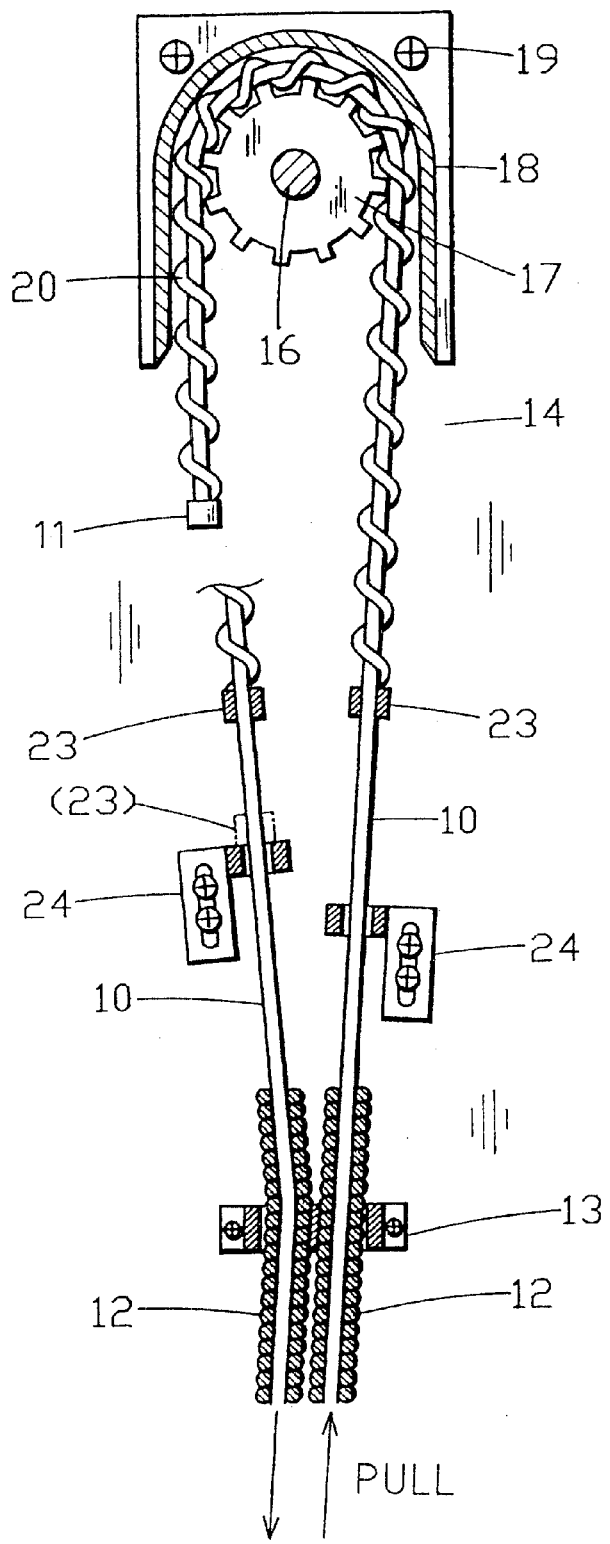
FIG. 6 is a sectional view of a bending control wire driving mechanism according to a second embodiment of the present invention.
Figure 7:
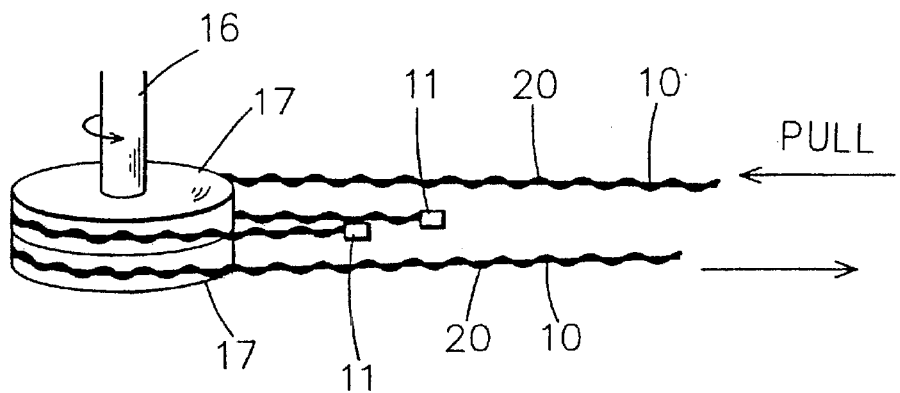
FIG. 7 is a perspective view schematically showing an essential part of the bending control wire driving mechanism according to the second embodiment of the present invention.

FIG. 6 shows a second embodiment of a bending control wire driving mechanism to which the present invention is applied. FIG. 7 is a schematic view showing an essential part of the second embodiment.

In this embodiment, two toothed wheels 17 are placed in side-by-side relation to each other and connected directly to a shaft 16 driven to rotate with the bending control knob 5. A pair of control wires 10 are placed along the toothed wheels 17, respectively, being curved in an approximately U-shape. The curved portion of each control wire 10 is wound approximately half around the associated toothed wheel 17.

A distal end tip 11 is secured to a free end of each control wire 10 on which no tractive force acts. In this embodiment, the free end of each control wire 10, to which the distal end tip 11 is secured, extends from the area of engagement with the associated toothed wheel 17 in a direction in which the control wire 10 is turned back in an approximately U-shape with respect to the pull direction of the control wire 10.

The arrangement of the rest of this embodiment is the same as in the first embodiment described above. Therefore, the same members or portions as those in the first embodiment are denoted by the same reference numerals, and a description thereof is omitted.

By virtue of the described arrangement, when the toothed wheels 17 are rotated by turning the bending control knob 5, the control wires 10 move axially as the teeth of the toothed wheels 17 move. Thus, one of the pair of control wires 10 is pulled, while the other is pushed out. Consequently, the bendable portion 3 bends at an angle corresponding to the amount by which one of the control wires 10 is pulled.

Because the free end of each control wire 10 extends from the area of engagement with the associated toothed wheel 17 in a direction in which the control wire 10 is turned back in an approximately U-shape with respect to the pull direction of the control wire 10, the bending control wire driving mechanism requires substantially no space for the bending operation above the toothed wheels 17. Accordingly, it is possible to ensure a sufficient length for the grip portion 1a of the control part 1.

It should be noted that two mechanisms as stated above may be combined together for use in a four-direction bending control device.

Figure 8:
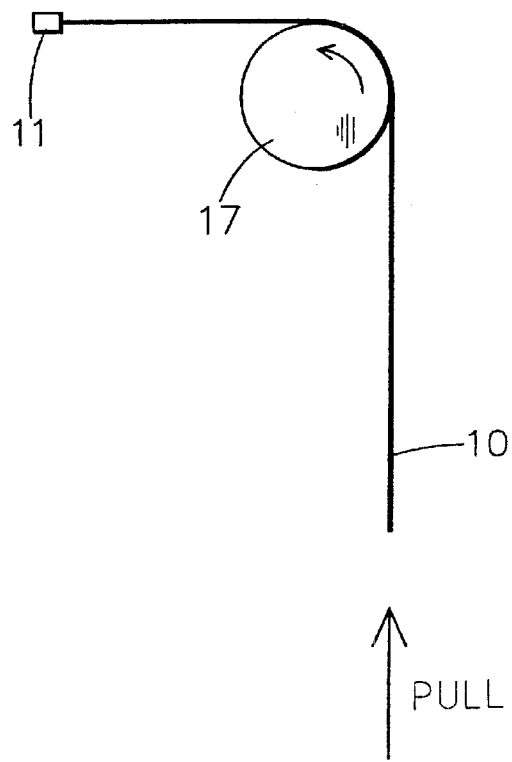
FIG. 8 is a schematic view of a modification of the bending control wire driving mechanism according to the second embodiment of the present invention.
Figure 9:
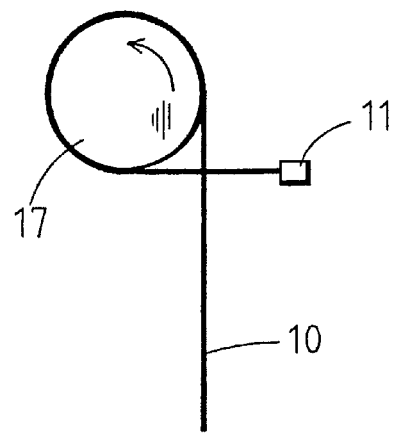
FIG. 9 is a schematic view of another modification of the bending control wire driving mechanism according to the second embodiment of the present invention.

Furthermore, the free end of each control wire 10 may extend from the area of engagement with the associated toothed wheel 17 in a direction perpendicular to the extension of the pull direction of the control wire 10, as shown schematically in FIGS. 8 and 9. The free end of each control wire 10 may extend in other directions. If the free end of each control wire 10 extends in a direction of not less than 90 degrees to the extension of the pull direction of the control wire 10, no space is needed above the toothed wheels 17.

Figure 10:
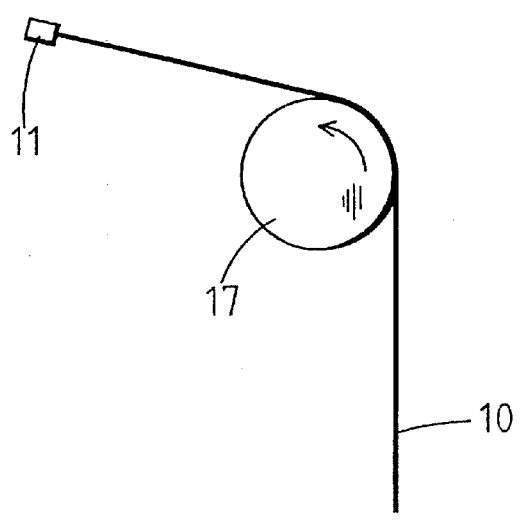
FIG. 10 is a schematic view of still another modification of the bending control wire driving mechanism according to the second embodiment of the present invention.

FIG. 10 shows an example in which the free end of a control wire 10 extends in a direction of less than 90 degrees to the extension of the pull direction of the control wire 10. In such a case, if the free end of the control wire 10 extends in a direction of not less than 45 degrees to the extension of the pull direction of the control wire 10, the space required above the toothed wheels 17 can be reduced on an effective level.

Figure 11:
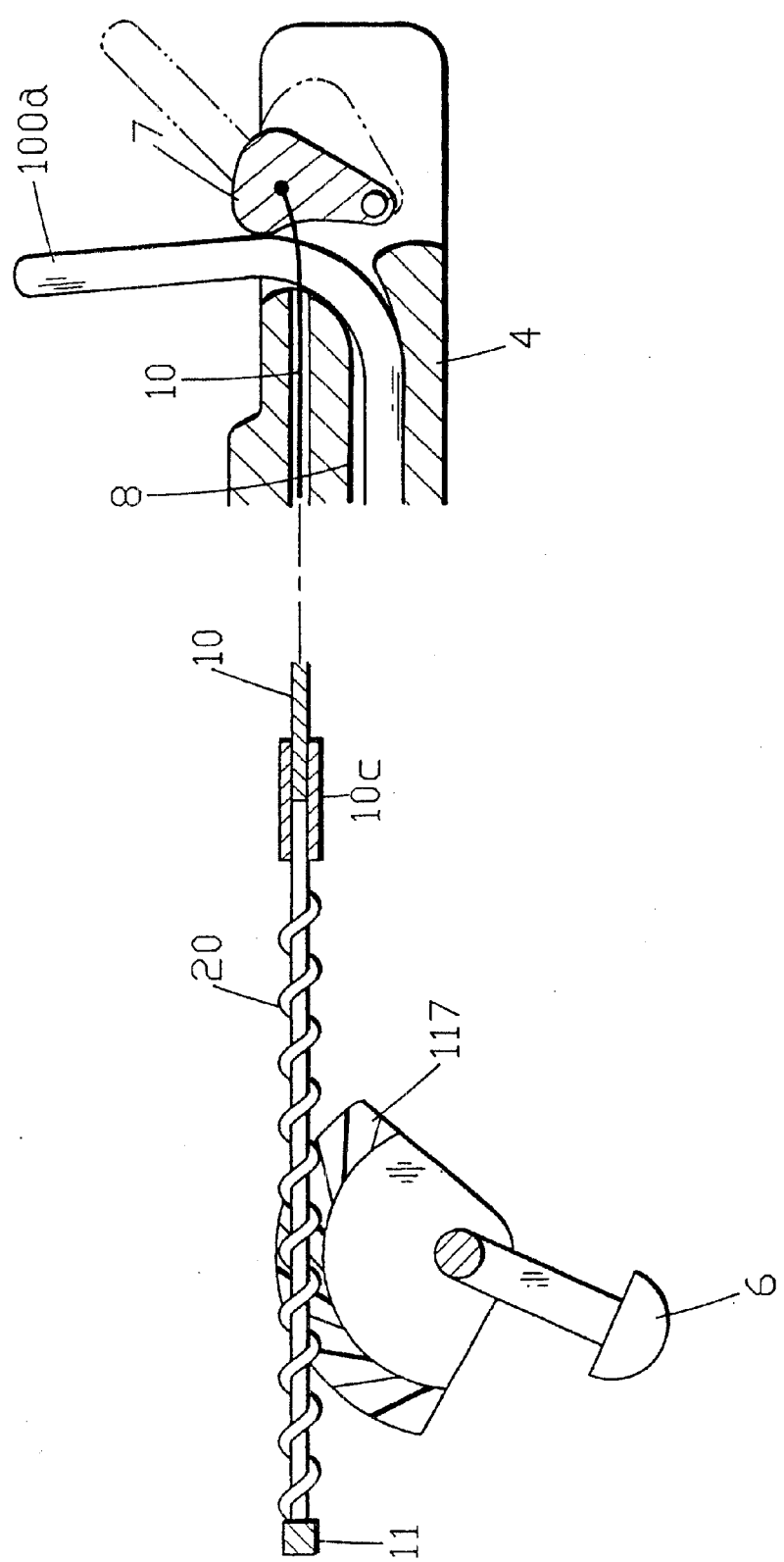
FIG. 11 is a sectional view of an erecting member control wire driving mechanism according to a third embodiment of the present invention, in which an intermediate portion of the control wire driving mechanism is omitted.
Figure 12:
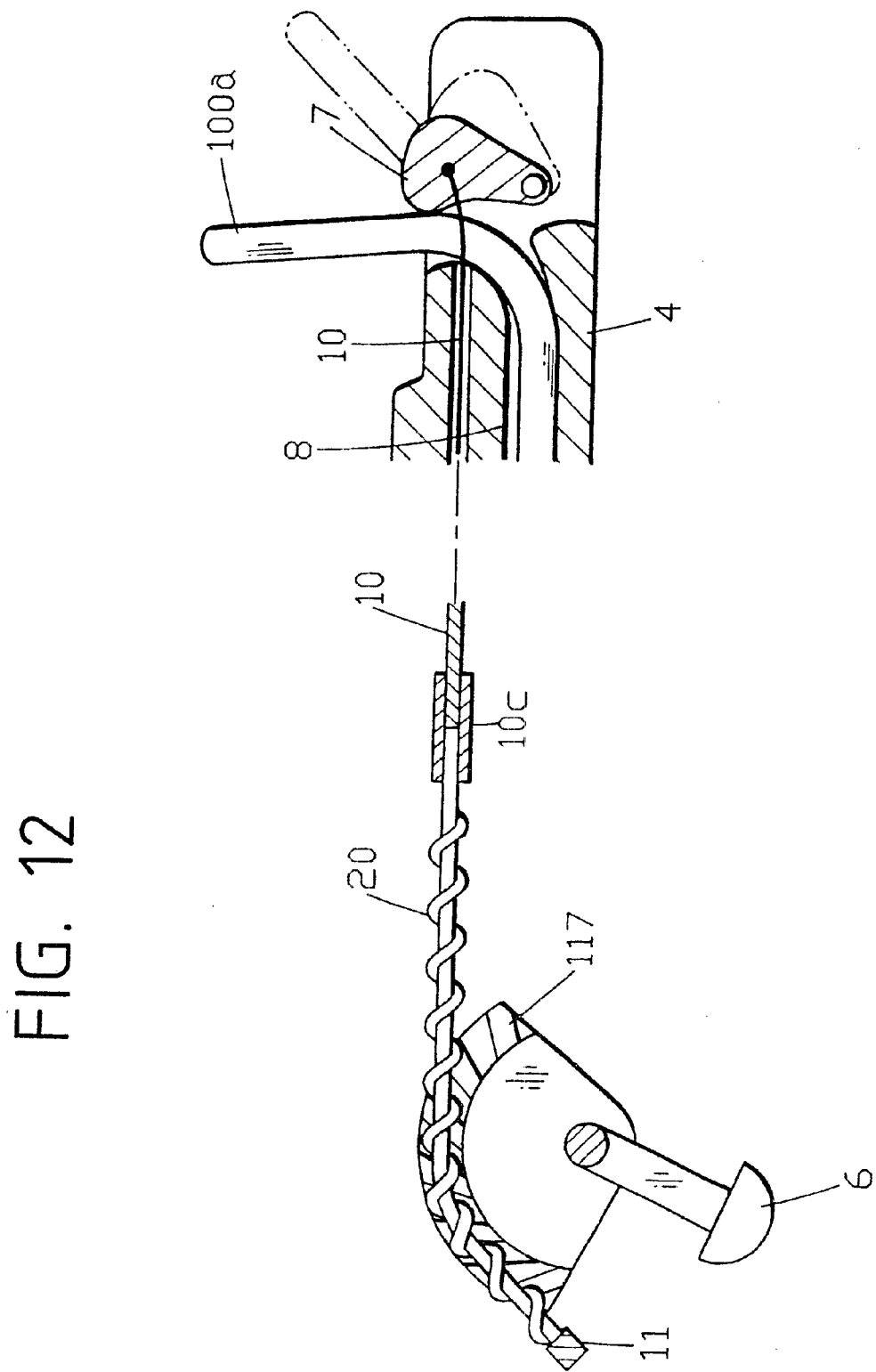
FIG. 12 is a sectional view of an erecting member control wire driving mechanism according to a fourth embodiment of the present invention, in which an intermediate portion of the control wire driving mechanism is omitted.

FIGS. 11 and 12 show an example in which the present invention is applied to a control device for a treating instrument erecting member 7 disposed in the distal end block 4. The treating instrument erecting member 7 is pivotally rotated by driving a single control wire 10 to advance or retract alone through a toothed wheel 117, whereby it is possible to change the direction of projection of the distal end portion 100a of the treating instrument 100 inserted in an instrument-inserting channel 8.

In the embodiments shown in FIGS. 11 and 12, a sector wheel 117 having teeth formed on a side surface thereof is connected to the erecting member control lever 6 and placed in the control part 1.

A single control wire 10 wound with a cord-like member 20 that meshes with the toothed wheel 117 extends in a straight-line form in the embodiment shown in FIG. 11. In the embodiment shown in FIG. 12, the control wire 10 is curved at the position for engagement with the toothed wheel 117. A connecting pipe 10c connects together two sections of the control wire 10.

Figure 13:
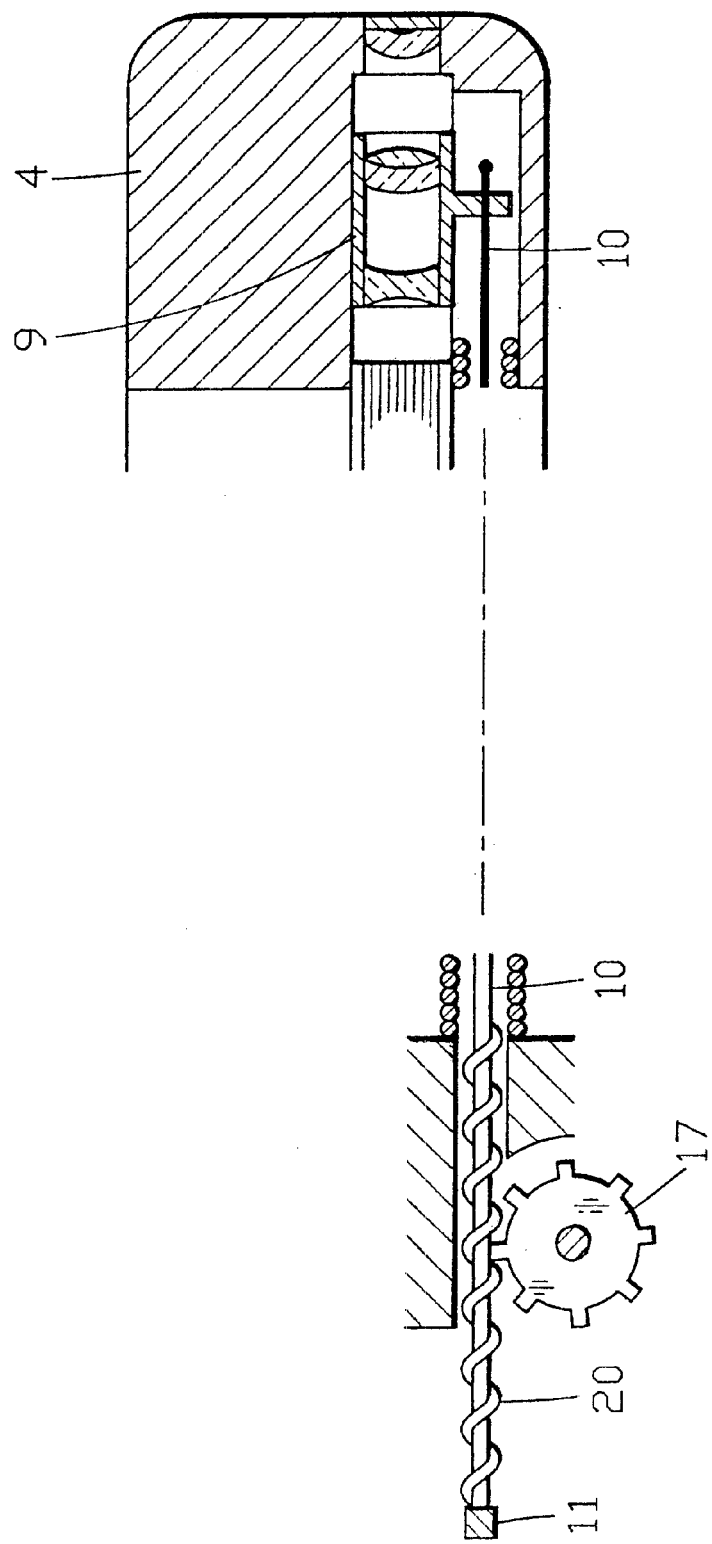
FIG. 13 is a sectional view of a focusing control wire driving mechanism according to a fifth embodiment of the present invention, in which an intermediate portion of the control wire driving mechanism is omitted.
Figure 14:
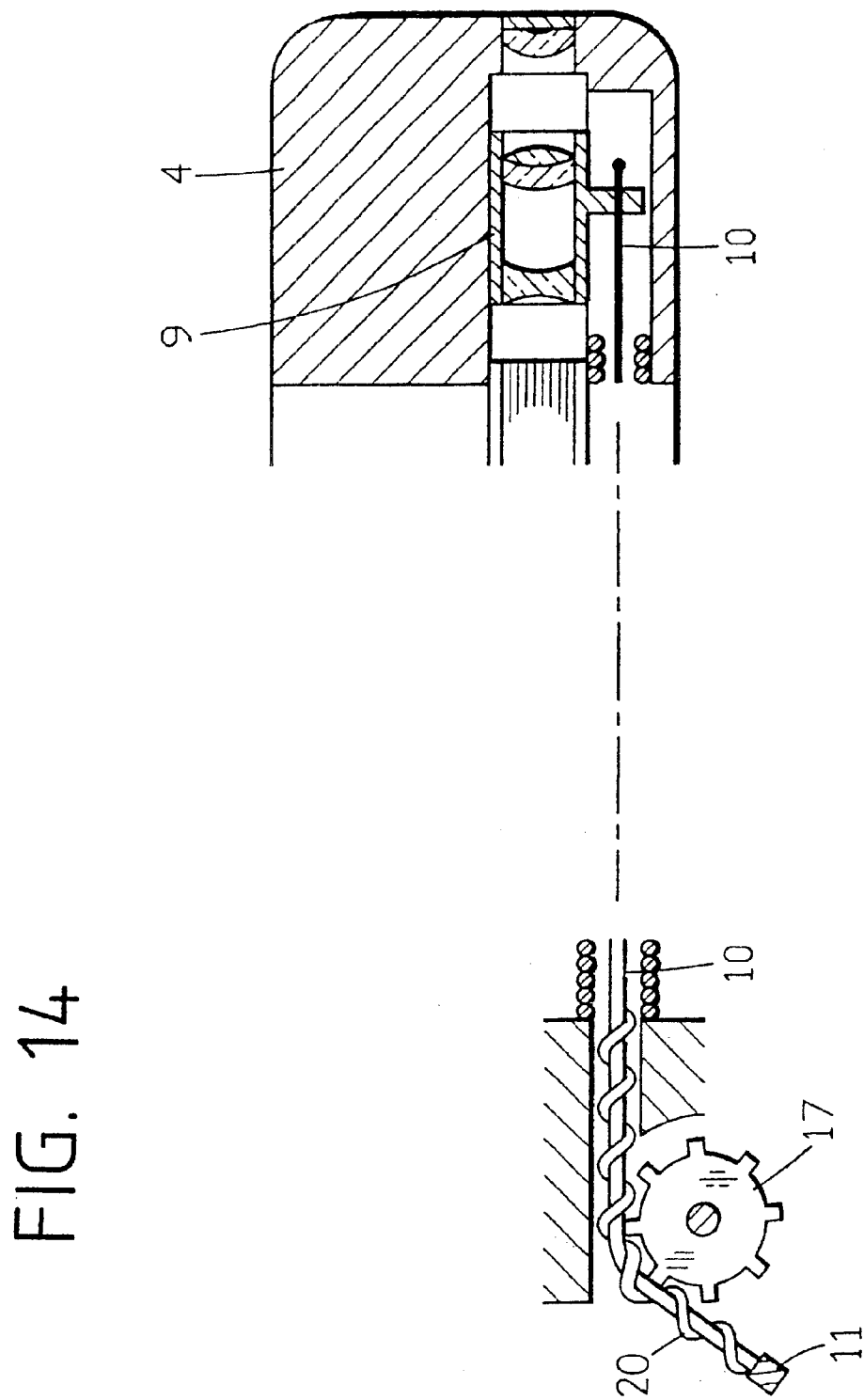
FIG. 14 is a sectional view of a focusing control wire driving mechanism according to a sixth embodiment of the present invention, in which an intermediate portion of the control wire driving mechanism is omitted.

FIGS. 13 and 14 show an example in which the present invention is applied to a focusing control device provided in an endoscope. An objective lens barrel 9 disposed in the distal end block 4 is advanced or retracted in the direction of the optical axis through a control wire 10, whereby focusing can be effected.

In these embodiments, a single control wire 10 disposed in the control part 1 is advanced or retracted in the axial direction by a toothed wheel 17 similar to that in the first or second embodiment.

According to the present invention, a toothed wheel for driving a control wire in the axial direction can be disposed at a position closer to the upper end of a control part of an endoscope. Therefore, it is possible to ensure a sufficient length for the grip portion of the endoscope control part and hence possible to attain favorable operability. In addition, because the control wire can be surely advanced or retracted with an extremely simple arrangement, it is possible to obtain a control wire driving mechanism for an endoscope that is superior in function despite a compact and lightweight structure and reduced cost.

While the invention has been described by reference to specific embodiments chosen for purposes of illustration, it should be apparent that numerous modifications could be made thereto by those skilled in the art without departing from the basic concept and scope of the invention.

What is claimed is:

1. A control wire driving mechanism for use in an endoscope comprising:
    a toothed wheel actuated to rotate in a control part of said endoscope; and
    a control wire having a cord-like member helically wound on and secured to an outer peripheral surface of a portion near a proximal end thereof at a pitch corresponding to a pitch of said toothed wheel, said control wire being meshed with said toothed wheel at said portion.

2. A control wire driving mechanism according to claim 1, wherein said control wire and said cord-like member are provided with respective coatings of a thermoplastic synthetic resin material, said coatings being welded together.

3. A control wire driving mechanism according to claim 1, wherein said toothed wheel has teeth formed obliquely in correspondence to a direction of said cord-like member helically wound on said control wire.

4. A control wire driving mechanism according to claim 1, wherein said toothed wheel has teeth formed on an outer periphery thereof.

5. A control wire driving mechanism according to claim 1, wherein said toothed wheel has teeth formed on a side surface thereof.

6. A control wire driving mechanism according to claim 1, wherein said control wire comprises a pair of control wires connected together at their proximal ends, said control wire being meshed with said toothed wheel in an approximately U-shape.

7. A control wire driving mechanism according to claim 1, wherein said control wire is a single control wire, said control wire being driven to advance or retract alone by said toothed wheel.

8. A control wire driving mechanism according to claim 7, wherein said control wire is meshed with said toothed wheel in a curved state along said toothed wheel, said control wire having a free end extending in a direction different from a pull direction of said control wire.

9. A control wire driving mechanism according to claim 8, wherein the free end of said control wire extends in a direction of at least 45 degrees to an extension of the pull direction of said control wire.

10. A control wire driving mechanism according to claim 8, wherein the free end of said control wire extends in a direction of at least 90 degrees to an extension of the pull direction of said control wire.

11. A control wire driving mechanism according to claim 8, wherein the free end of said control wire extends in a direction of at least 180 degrees to an extension of the pull direction of said control wire.

* * * * *